(12) United States Patent
Ikku et al.

(10) Patent No.: US 6,924,481 B2
(45) Date of Patent: Aug. 2, 2005

(54) SCANNING MICROSCOPE WITH BRIGHTNESS CONTROL

(75) Inventors: Yutaka Ikku, Chiba (JP); Tetsuji Nishimura, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/158,356

(22) Filed: May 30, 2002

(65) Prior Publication Data

US 2002/0185597 A1 Dec. 12, 2002

(30) Foreign Application Priority Data

Jun. 8, 2001 (JP) .......................................... 2001-173979

(51) Int. Cl.$^7$ .............................................. G01N 23/00
(52) U.S. Cl. ........................ 250/310; 250/304; 250/307
(58) Field of Search .......................... 250/304, 306–310, 250/311

(56) References Cited

U.S. PATENT DOCUMENTS

| | | | | |
|---|---|---|---|---|
| 5,051,585 A | * | 9/1991 | Koshishiba et al. | ........ 250/306 |
| 6,365,897 B1 | * | 4/2002 | Hamashima et al. | ........ 250/310 |
| 6,479,819 B1 | * | 11/2002 | Hamashima et al. | ........ 250/310 |
| 6,555,816 B1 | * | 4/2003 | Sawahata et al. | ........... 250/310 |

* cited by examiner

*Primary Examiner*—John R. Lee
*Assistant Examiner*—Paul Gurzo
(74) *Attorney, Agent, or Firm*—Adams & Wilks

(57) ABSTRACT

Automatic pattern matching and shape measurement are enabled by adjusting a brightness level of a microscope image based on information of a local region of the image so that a magnified image of the local region takes on an appropriate brightness and is not affected by brighter peripheral portions of the image, thereby enabling feature extraction of a desired pattern. By using the inventive method in an energized beam apparatus having a sample stage capable of linear and tilting movement, a series of operations including cross section forming, sample tilting, cross section observation, and pattern recognition, may be performed on an automated basis.

10 Claims, 4 Drawing Sheets

3 ION OPTICAL SYSTEM
CONDENSER LENS
BEAM BLANKER
ALIGNER
APERTURE
OBJECTIVE LENS

VARIOUS CONTROL SIGNALS
ACCELERATION VOLTAGE
ION OPTICAL SYSTEM
DEFLECTION SCAN
GAS SUPPLY
SAMPLE STAGE DRIVE

HIGH MAGNIFICATION
CROSS SECTION IMAGE

BEFORE ETCHING

AFTER HOLE EXCAVATION

SURFACE FINISHING PROCESSING

3 ION OPTICAL SYSTEM
  CONDENSER LENS
  BEAM BLANKER
  ALIGNER
  APERTURE
  OBJECTIVE LENS

VARIOUS CONTROL SIGNALS
  ACCELERATION VOLTAGE
  ION OPTICAL SYSTEM
  DEFLECTION SCAN
  GAS SUPPLY
  SAMPLE STAGE DRIVE

SCANNING MICROSCOPE WITH BRIGHTNESS CONTROL

BACKGROUND OF THE INVENTION

The present invention relates to brightness control technology on a scanning electron microscope having a function of automatically executing shape measurement of a pattern within an image, and more particularly relates to brightness control technology suitable for a focused ion beam device provided with a function of automatically executing shape measurement of a pattern formed in cross section by cross section machining.

A focused ion beam device such as that shown in FIG. 4 is used when observing the internal structure of samples such as the internal structure of a semiconductor device, and after performing slicing to expose a cross section the cross section is observed as a scanning microscope image. Specifically, since focused ion beam devices can be used for microscopic observation of material processing, in recent years they have often been used in carrying out cross sectional machining and observation of samples. The cross sectional size is generally about a few $\mu$m to a few tens of $\mu$m. Ions from an ion source 1 are formed into a beam shape by an ion optical system 3, and the ion beam 2 is received through operation of a deflector 4 and irradiated to specified locations on a sample 9. This focused ion beam device provides a scanning ion microscope function, a sputter etching function and a maskless deposition function. Charged particles called secondary ions or secondary electrons ejected by the sample due to irradiation of an ion beam scanned by the deflector 4 are detected by a secondary charged particle detector 6, which functions as a scanning ion microscope by making this detection value correspond to an irradiation position and producing a corresponding image. A sputtering function is achieved by causing sputtering and dispersal of sample material at portions where an ion beam positioned by the deflector 4 is irradiated. In addition, a deposition function is also realized for irradiating a focused ion beam 2 while forming a layer of the material while spraying source material gas from a gas gun 6 to cause formation of a layer of the material at the irradiation position. In a basic slicing sequence using this type of focused ion beam device, as shown in FIGS. 3A–3B, locations within a sample where the cross section is to be observed are first specified.

In order to observe the cross section, it is necessary to make a wide opening in front of the cross section part (the section enclosed by the dotted line). This is the reason that in obtaining a microscopic image of the cross section it becomes necessary to beam scan from a steep angle with respect to the cross section. If a processing region is specified, coarse processing is carried out using an ion beam from a direction vertical with respect to the sample surface, as shown in FIG. 3B. Since this processing is more to machine a hole required for observation than to expose an observation cross section V, rough sputtering using a heavy current beam results, and the observation cross-section V is damaged as shown in FIG. 3B. This sputtering operation can be accomplished with high etching efficiency by spraying assist gas from the gas gun 6 and causing evaporation of the sputtered material using the assist gas. The observation cross section is polished by carrying out etching with a reduced beam current after drilling has been completed, and a neat cross section as shown in FIG. 3C is then exposed. A sample platform after this pretreatment is tilted and beam scanning is performed so as to irradiate an ion beam from a steep angle with respect to the cross section, to obtain a scanning ion microscope image of the cross section to be observed.

However, a display 11 for showing the microscopic image is incorporated into this type of focused ion beam device, and in order to make it easy to view the microscopic image a function for automatically adjusting brightness so as to make brightness information for an overall image a specified average brightness level in the observation field of view is provided in a computer 10. With this function, it is easy to see the entire image on the display, but in the event that an evaluation is made regarding the shape of a pattern formed on the cross section to be observed, there are problems that it is not possible to make out features of a noted pattern because the image at parts of the cross section where the noted pattern exists is either too dim or too bright. This phenomenon is more noticeable when the occupancy rate of the cross section in the observational field of view is low. However, in the case of this cross sectional observation, as described previously, first of all an ion beam 2 is irradiated from above the sample and pretreatment to drill a hole in front of the cross section to be observed is required, and a cross section image is obtained by tilting a sample stage 7 after the slicing processing to scan the ion beam across the sample from a steep angle. Movement of this sample stage 7 is a main cause of field of view slippage when using a microscope at high degrees of magnification. The microscopic image at the time of tilt drive is acquired at a comparatively low magnification factor. The occupancy rate in the observational field of view of the sectioned part constituting a subject of observation becomes low in that case, and a phenomenon occurs whereby it is not possible to observe a noted pattern without appropriate brightness control of the subject image. If it is not possible to observe a pattern, a noted pattern will be perceived in the center of the microscope image while confirming position, making it impossible to perform shape measurement at a high magnification factor.

Also, in slicing of a sample using a conventional device and shape measurement of the slice section pattern, a sequence of operations from slicing before observation to conformation and position adjustment of a noted pattern and shape measurement of the noted pattern must be carried out one at a time by an operator with the focused ion beam device each time, even for a fixed task, which poses a problem with regards to working efficiency. In particular, with tasks for a sample having a repeating pattern structure, there is a lot of repeating of exactly the same tasks, which is stressful to an operator.

SUMMARY OF THE INVENTION

The present invention provides a focused ion beam device that can automatically carry out pattern matching and shape measurement by adjusting brightness level of both microscope images on a display so that an observation region becomes an appropriate brightness without being affected by brightness of peripheral images within the field of view, so as to be able to effectively carry out feature extraction of a noted pattern. Also, a system is provided where, in the case of carrying out fixed shape measurement, it is not always necessary for an operator to be manning the system to carry out a series of operations.

Brightness adjustment in a scanning electron microscope of the present invention enables display of an image within a designated region at an appropriate brightness without being affected by peripheral images within the field of view, by providing means for designating a desired region within a microscope image, means for designating average brightness of an image within the designated region, and means for adjusting overall brightness of a microscope image based on an amount of brightness control designated.

Also, by providing a sample stage drive mechanism capable of at least two dimensional movement and inclination alteration, means for executing a series of slicing processing and noted pattern access programs from slicing machining to sample stage tilting and sliced section microscope image acquisition, and means for carrying out noted pattern shape measurement in line with the programs, it is made possible to automatically measure the shape of a pattern formed at the sliced section of the sample.

PREFERRED EMBODIMENTS OF THE PRESENT INVENTION

Figure 1A:
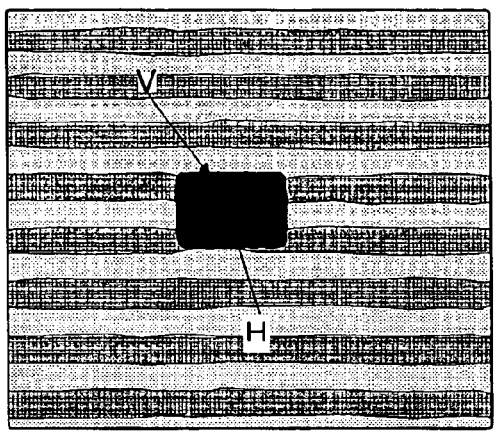
FIGS. 1A–1F are drawings showing microscope images when the present invention is applied to pattern shape measurement of a sliced section using a focused ion beam device, in chronological order.
Figure 1B:
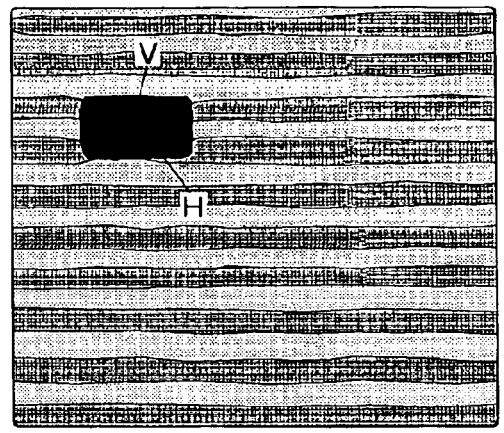
Figure 1C:
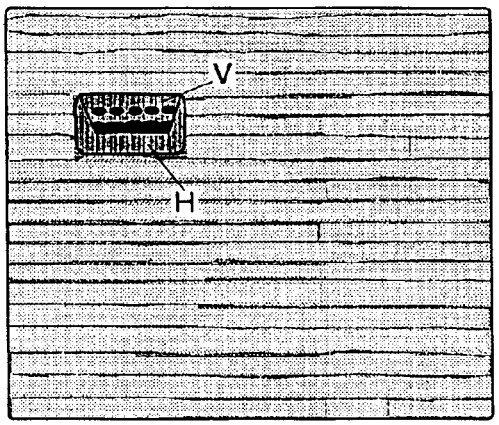
Figure 3A:
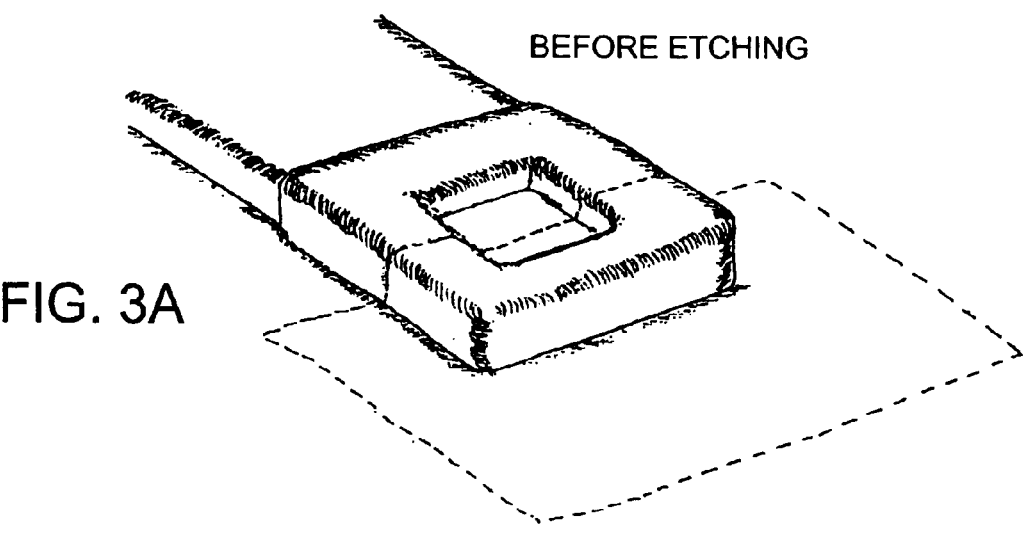
FIGS. 3A–3C are drawings for description of slicing processing using a focused ion beam device.
Figure 3B:
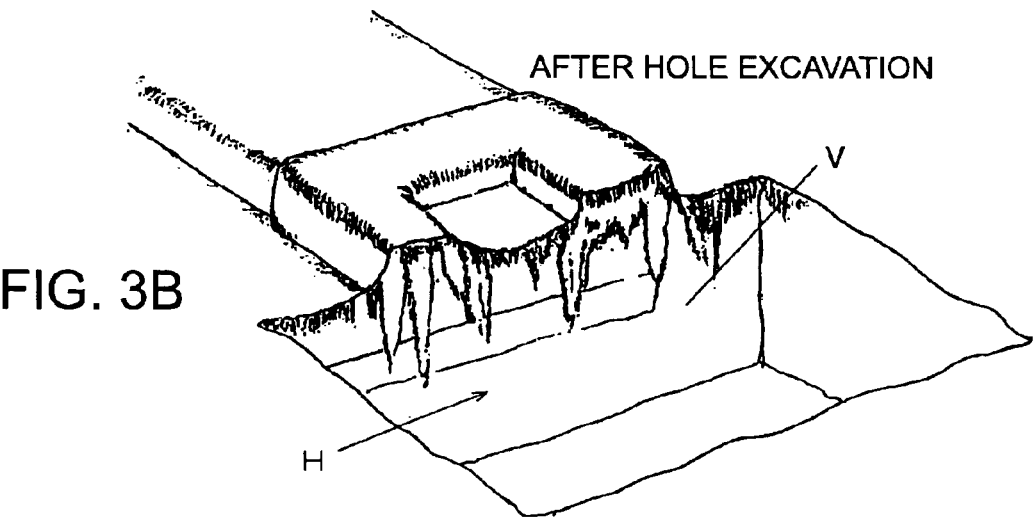
Figure 3C:
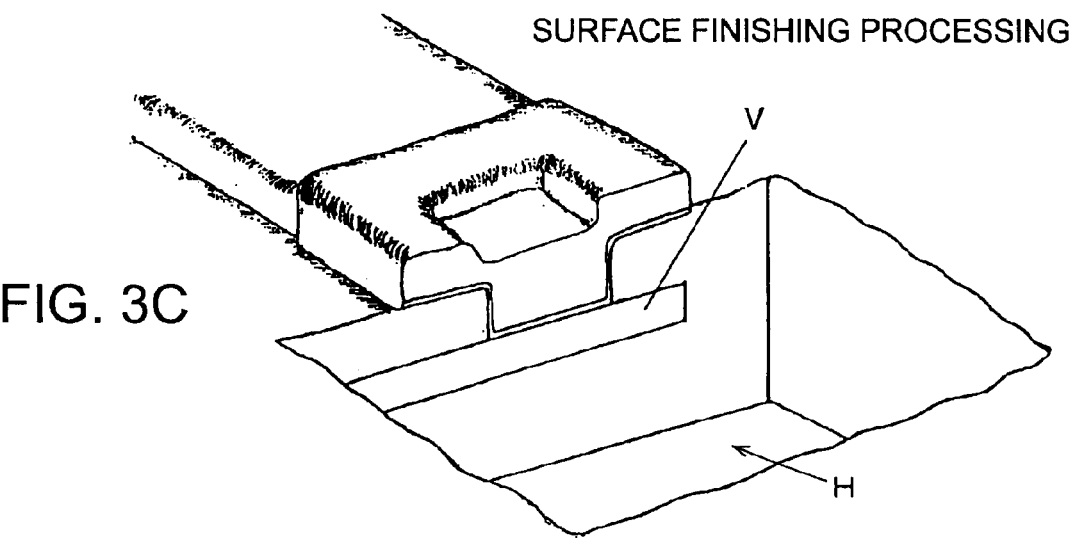
Figure 4:
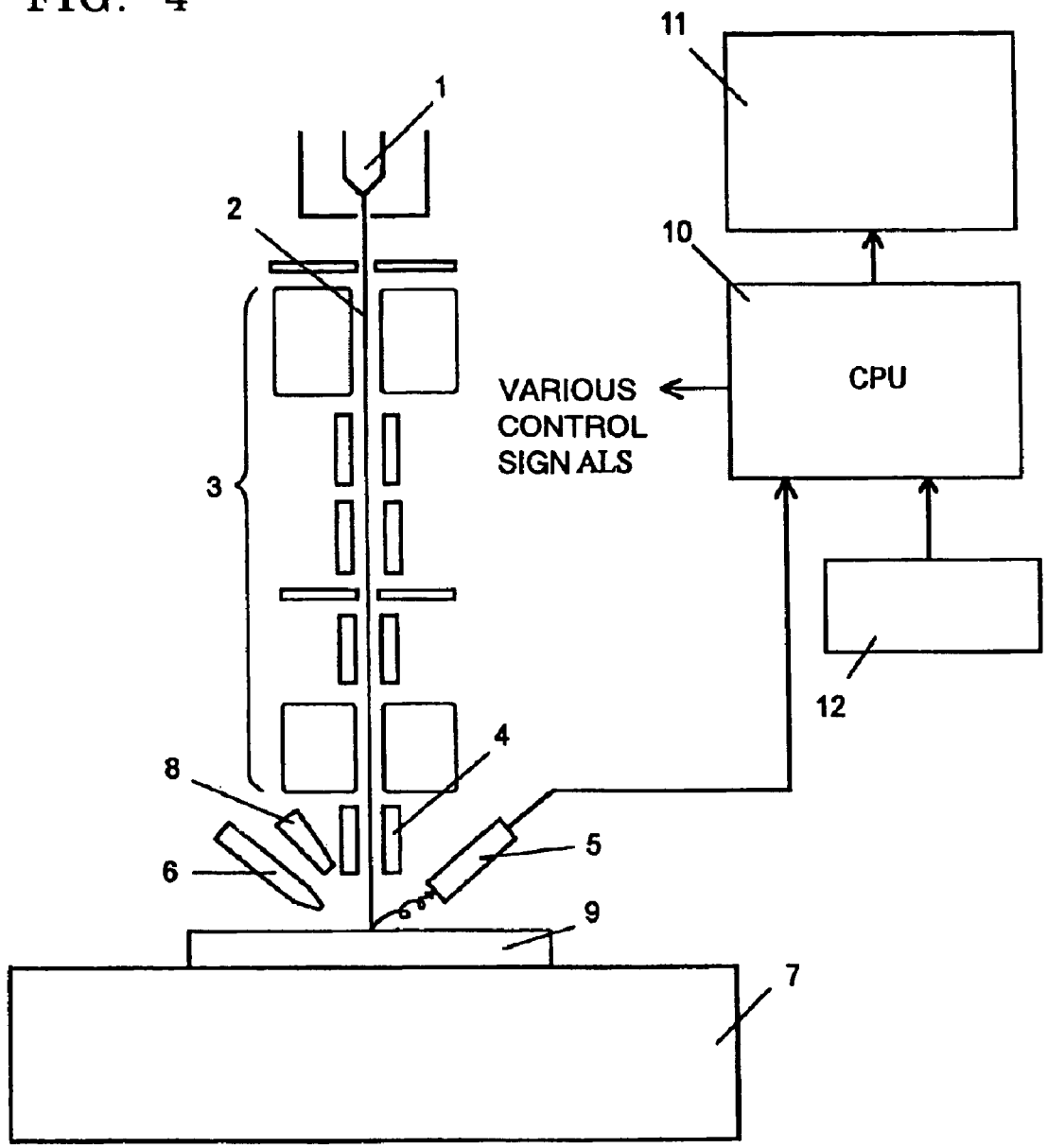
FIG. 4 is a drawing showing the basic structure of a focused ion beam device.

In the case of using a focused ion beam device capable of confirming machining of a sample and the machined shape in a microscope image to observe the structure inside the sample, first of all machining is carried out to expose a section of the sample. As shown in FIG. 3C, a hole H is formed in front of an observation sliced section V, and the observation sliced section V is finished off to a smooth appearance. The sample at this time has a scanning microscope image from above that appears as shown in FIG. 1A. In a focused ion beam device, an automatic brightness adjustment function adjusts the form of the sample within the observational field of view to a form that is easy to see overall. However, as shown in FIG. 1A, a display image of a sliced section V, being an object of observation in this case can not observe the existence of a dark noted pattern P. In order to obtain a microscope image of this sliced section where a hole has been formed, it is necessary to carry out ion beam scanning from a steep angle, and the sample surface must be tilted by driving the sample stage. A microscopic image obtained in this tilted state is shown in FIG. 1B. Movement of the sample naturally follows movement within the microscope field of view, and at that time the microscope magnification factor is set low in order to avoid the subject region moving out of the field of view. This means that the occupancy rate in the observational field of view of the region that is the subject of observation is low, and an automatic brightness control function does not function with respect to this subject of observation. For example, as shown in FIG. 1B, it is not possible for a display image of the sliced section to observe the existence of a dark noted pattern. With the present invention, the automatic brightness control function is suspended in this state, and brightness adjustment is carried out so as to be able observe the sliced section X being the subject of observation. A display image that has had brightness control corrected is shown in FIG. 1C, and has an appearance that enables observation of the sliced section V. On the other hand, an image of a peripheral sample surface occupying a large part of the observational field of view is indistinct.

Figure 1D:
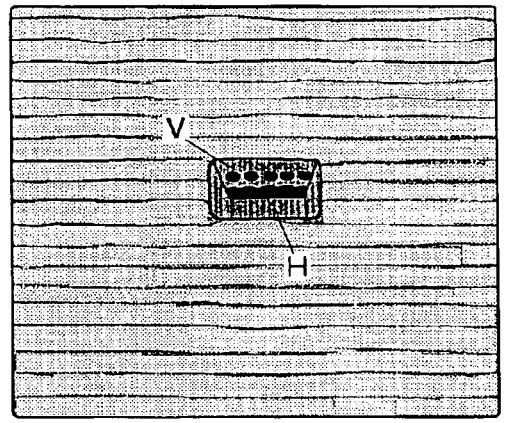
Figure 1E:
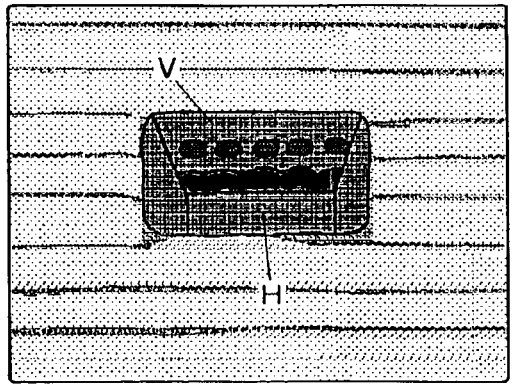
Figure 1F:
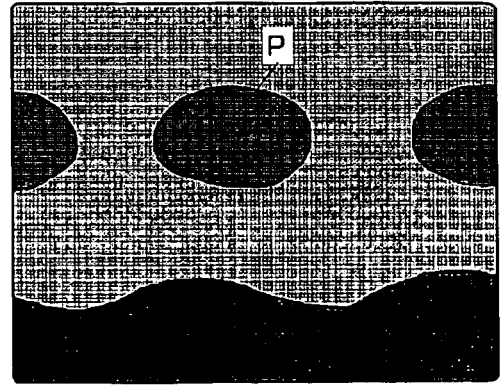

Depending on the situation, halation may arise. However, since the subject of observation is clear, the lack of clarity at the peripheral images does not pose that much of a problem. As shown in FIG. 1D, the sample stage is moved in two dimensions, the sliced section, being the observation region, is position adjusted to be in the center of the observational field of view, and the magnification factor of the microscope image is increased, as shown in FIG. 1E. At places where it is possible to observe patterns within the sliced section, it is possible to perform a comparison with template images, being standard patterns, by performing matching with the template images, to carry out positional adjustment and access to a noted formed pattern to make it possible to acquire an image at a high magnification factor. Because of the high magnification factor image, shape measurement and evaluation etc. of the noted pattern are achieved, and when fine positional adjustment at this time can not be handled by the sample stage drive mechanism 7 it is handled by a deflection bias function of the defector 4 of the microscope. Pattern shape measurement is carried out with this high magnification factor, and it is important that brightness control for the microscope image in this state is appropriate to give a clear image. If brightness control carried out at the stage shown in C is finally corrected when there is no optimum brightness control at the F stage, that amount of brightness control is stored as an optimum amount of brightness control for shape measurement with respect to this sample, and applied to the next and subsequent measurement.

The present invention is also intended, in slicing and sliced section pattern shape measurement of a semiconductor device etc. having repeating patterns formed inside a single sample, to improve the drawback where the same sequence of operations from slicing before observation to confirmation and position adjustment of a noted pattern and shape measurement of the noted pattern must be carried out one at a time by an operator with the focused ion beam device each time. In automatic machining of a cross section, conventionally, if data for depth and length of a hole in front of the sliced section was input, a function to enable processing without requiring the operator to repeat operations from course processing to sliced section finishing was provided, but with the present invention, if the positions of a number of slice processing sections are further designated, a function is provided whereby slicing and shape measurement of repeating patterns can be executed sequentially without the operator being in constant attendance.

An ion beam 2 emitted from a lens barrel of a focused ion beam device provided with ion beam current value switching means is irradiated onto a sample 9 mounted on a sample stage 7. Secondary charged particles are generated by this irradiation, captured by a secondary charged particle detector 5, and the strength of the secondary charged particles is taken in to a computer 10, and then the sample image is displayed on a display 11 together with device information. A gas gun 6 is controlled by the computer 10, and by irradiating an ion beam 2 while a source material gas is being sprayed against the sample a protective film can be formed on the sample 9 due to ion beam assist. The computer 10 has a function to program the following actions, and a function to execute that program.

Step 1: Moving the sample stage to the sample objective position. At this time, since an observation region is specified from a microscope image of the sample surface at a comparatively low magnification factor, brightness control of the display is carried out by validating a normal automatic brightness control function.

Step 2: Next, a protective film is formed on the sample surface by irradiating a focused ion beam 2 while spraying deposition source material gas using a gas gun 6. This is to prevent surface sections of the observation section being etched by the ion beam at the time of slicing. If the ion beam electrical current value at this time becomes large, the protective film will not be formed and there will be etching of the sample, and so setting of the beam current value is critical.

Step 3: Next, the sample is etched by switching the ion beam current to a large value to partially irradiate the focused ion beam, and form a cross section perpendicular to the sample surface. Once this coarse excavation is completed, beam current is lowered and a sliced section that is prone to damage is subjected to finishing processing.

Step 4: Next, the sample stage 7 is tilted to enable observation of the formed cross section, and the ion beam current value is constricted using means for switching ion beam current, to acquire a microscope image.

Step 5: In the event of initial measurement (generally at the time of a prior test), the automatic brightness control mechanism of the device functions so that the image of the sliced section V, being the observation region, is not at an appropriate brightness, as shown in FIG. 1B, and so the automatic control function is cancelled, the observation region is manually adjusted to an appropriate brightness and the image of the sliced region V becomes a suitable brightness, as shown by FIG. 1C. For second and subsequent measurements (generally at the time of actual testing), a microscope image can be immediately obtained at this stage because the amount of brightness control is changed to that set during the initial measurement.

Step 6: A pattern image of the sliced section and template images are subjected to pattern matching, and position adjustment of a sample is carried out based on this positional information, the magnification factor of the microscope is increased, and a noted pattern P is displayed in the center of the display screen at a high magnification factor.

Step 7: Shape measurement is carried out for a pattern formed at the sliced section, such as pattern comparison between a noted pattern P specified based on a template image and a formed pattern, and size measurement for pattern feature information extracted from the screen.

By storing the above steps as a plurality of programs, a person operating the scanning ion beam microscope can execute a single program already created for the purpose of processing a sample currently mounted on the sample stage. Once program execution has started, with the example described above, it is possible to execute from step 1 to step 6 without human intervention.

In the case of a sample 9 having repeating patterns, there is also a function to cause execution of a program repeating from step 1 to step 7 at a plurality of locations. For this reason, even if there is no person manning the scanning ion microscope, it is possible to carry out pattern shape measurement for a plurality of cross sections of the sample.

A description has been given above of the present invention assuming a focused ion beam device, but the technical concept of the present invention can also be applied directly to a scanning electron microscope, except for the points relating to protective film formation using deposition.

EXAMPLE 1

An example will be given of executing pattern measurement for a sliced section V with a DRAM used in a system of the present invention as a sample. Initially, program setting is carried out for the position of a sliced section V to be processed, and for what type of shape measurement is to be performed for that sliced section. In the system of this example, basic software for carrying out pattern measurement for the sliced section V is provided, and parameters and conditions are set according to this software. In order to initially acquire an image for carrying out shape measurement, in the case of cross sectional observation the sliced section after making a cross section is displayed as a microscope image at a desired observational magnification factor. Places where cross sectional observation will take place are specified from the displayed image, and positional information for these places is input to a computer, but start and end points are specified using position specifying means on the screen such as a mouse, and a reference line designating sliced section positions is set on microscope screen coordinates. If there is a sample for which shape measurement can be specified from the display screen, it is not necessary to create a cross section and operations subsequent to the display image are executed, but here a description will be given focusing on cross section shape measurement.

If sliced section position information is input, operational content is set. The basic program in this case is set up in a system of the present invention, and at the time of performing individual measurements a sample that is the subject of observation is handled and the parameters and actual data for that handling are set. Incidentally, in the slicing processing in this example, with respect to the size of the hole H in front of the sliced section, since the width and depth are input these values are input and set.

Continuing on, a noted pattern P within that cross section is specified, and content of shape measurement to be executed for the noted pattern P is set. Specification of the noted pattern P is carried out by designating a partial region of a template image, and content of the shape measurement is feature extraction of the noted pattern, distance between two specified points, center positions of two points, distance between two specified lines, angle formed by two lines, crossing positions of two lines, and length of a perpendicular line lowered down from a line from a particular point. Required items among these setting items are sequentially set and registered. Other tasks are included in prior program setting operations.

If prior program setting operations have been completed, the focused ion beam device is operated and slicing processing and shape measurement of the sliced section are carried out. First of all, in step 1, the position of the sample is adjusted with respect to the microscope so that it is possible to irradiate an ion beam to places having the same structure as previously set shape measurement sections. Next, in step 2, the focused ion beam 2 is irradiated while spraying phenanthrene, being a deposition source material gas, using a gas gun 6, to form a carbon protective film on the sample surface so that the surface of the sliced section is not damaged by sputter etching. In step 3: the sample is etched by switching the ion beam current to a large value to partially irradiate the focused ion beam, and form a cross section perpendicular to the sample surface, but the size of a hole at this time is based on a previously set value. Once this coarse excavation is completed, beam current is lowered and a sliced section that is prone to damage is subjected to finishing processing. Respective beam current values at this time are set in advance by a basic program, but it is possible to alter these values as required. After slicing processing is completed, in step 4, the sample stage 7 is tilted to enable observation of the formed cross section, and the ion beam current value is constricted using means for switching ion beam current, to acquire a microscope image. In step 5, the brightness control function for the display is changed over. Specifically, the automatic brightness control function at this stage for transition of the observation subject from the sample surface to the sliced section is suspended, and a fixed amount of brightness adjustment is switched to give the sliced section image an appropriate brightness. Once slicing processing is completed, and up until the subject is moved to the sliced section, the microscope image is at a low magnification factor and the subject of observation is the surface of the sample in a comparatively wide range, which means that brightness control of the display involves an automatic brightness control function based on image information for the entire screen and functions appropriately for the overall screen, but there is not appropriate brightness control for the image of the sliced section. This fixed adjustment amount that can be switched is set in advance in a program using an optimum brightness control amount, obtained experimentally in a test executed beforehand for the same kind of sample. This switching of the brightness control is the main feature of the present invention, and as a result it is possible to smoothly implement the operation of the next step in a system. It is also possible to cause this optimum brightness control amount to be learnt as a relative brightness variation amount and incorporated as a function for automatic adjustment. In step 6, a pattern image of the sliced section and a template image are subjected to pattern matching, and position adjustment for the sample is carried out based on this positional information, the magnification factor of the microscope is increased, and a noted pattern is displayed in the center of the display screen at a high magnification factor.

This template image is a microscope image of a cross section shape measurement section previously acquired in a prior program setting operation. The noted pattern can be specified by designating a partial region of this template image. In step 7, features are extracted for a specified noted pattern, and sequential measurement is carried out for previously set shape measurement items, with this data then being stored in a memory section. With respect to the actual method of shape measurement, this known method is not the main point of the present invention and so detailed description has been omitted. Following the above described steps, machining of the sliced section and shape measurement are completed for one place.

Figure 2A:
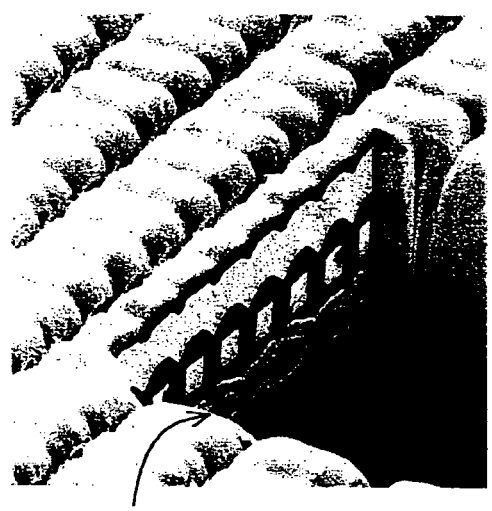
FIGS. 2A–2D show comparative images showing differences between microscope images using switched brightness control function of the present invention, with a DRAM as a sample.
Figure 2C:
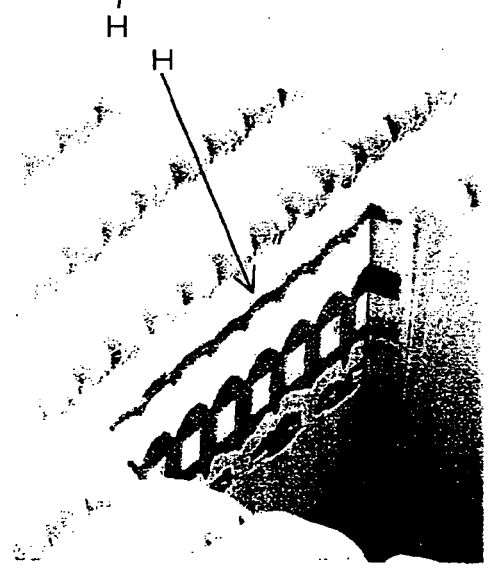
Figure 2B:
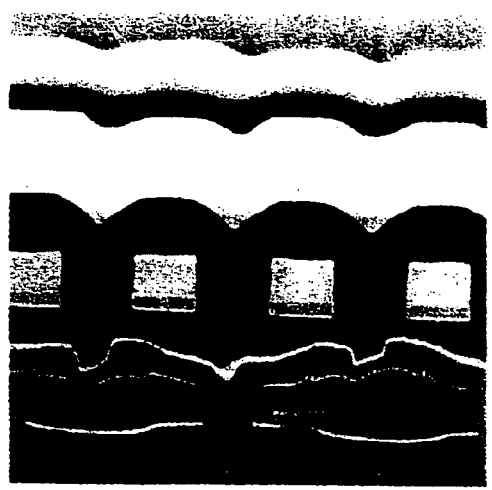
Figure 2D:
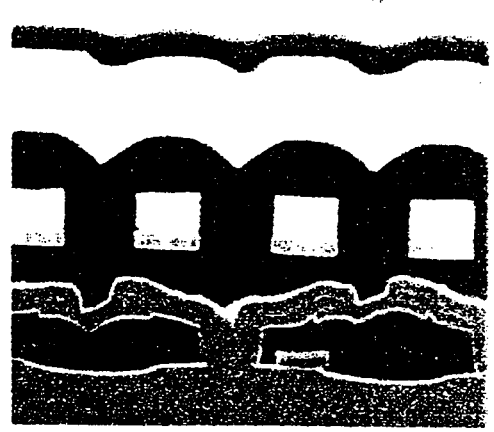

Microscope images of a DRAM constituting a sample of this example are shown in FIGS. 2A–2D. On the left side of the drawing, FIG. 2A and FIG. 2C are microscope images taken from diagonally above and to the left of a cross section at a point in time after completion of slicing processing, while FIG. 2B and FIG. 2D on the right side are high magnification factor microscope images taken of a noted pattern from diagonally above and in front at a high magnification factor.

The upper of the two drawings, A and B, are images taken when the automatic brightness control function is operating, while the lower two drawing, C and D, are taken with an amount of brightness adjustment that gives an appropriate brightness for the sliced section image. As will be clear from comparison of these images, with the upper of the two images it is possible to clearly observe the images of the sample surface but it is not possible to observe a pattern of the sliced section, while with the lower images it is not possible to clearly observe the images of the sample surface but it is possible to distinctly observe patterns of the sliced section.

In this embodiment, the sample is a DRAM formed with repeating patterns, and shape measurement for each of the sliced sections is carried out in the same way, which means that one program is sufficient for use in machining and shape measurement. The same processes are repeatedly executed corresponding to a previously set reference line position. In the case of this embodiment, if cross section locations constituting subjects of measurement are initially registered as reference line positions, the content of shape measurement will be the same for each cross section, which means that it is likely that there will be an interruption in the event that a microscopic image is obtained midway, as required, but it is possible to execute a series of operations almost completely automatically. Firstly, even if a plurality of cross sectional observations are made for a single sample, in the event that each cross section has a different pattern, operations for each cross section progress sequentially in accordance with a different program set for each different pattern, and it is not normally necessary for an operator to be there to carry out operations. With the system of the present invention, a set program can be stored in a storage medium, and can be used directly in the same types of measurement executed subsequently, and an editing function for partially changing setting can also be provided. Also, with the above described embodiment, a fixed brightness control amount after switching the brightness control function was set using a test value obtained through a prior test, but it is also possible to have a structure for adjusting the sliced section image to an appropriate brightness by switching an adjustment amount so as to perform automatic adjustment based not on information detected from an overall screen but on image information detected from the sliced section area while continuing the automatic brightness control function.

A brightness control method for a scanning electron microscope of the present invention carries out brightness adjustment for a microscope image to be displayed on a display based on image information of an observation region when the observation region of a sample specified on a low magnification factor image is displayed at a high magnification factor, and a scanning electron microscope of the present invention incorporating this into a system comprises, means for automatically adjusting brightness of a microscope image to be displayed on a display from overall image information, brightness control means for designating an average brightness of a specified region, and means for suspending the function of the automatic brightness control means and controlling overall brightness of the microscope image based on a specified amount of brightness control, thus making it possible to display an image within an observation region at an appropriate brightness without being affected by the image at the periphery of the field of view when displaying an observation region of a sample specified on a low magnification factor image at a high magnification factor, and so it is made possible to handle template images because an image of a sliced section is obtained at an appropriate brightness when the observation region is moved into the sliced section region, enabling pattern matching.

Also, by providing the scanning electron microscope of the present invention with a sample stage drive mechanism capable of moving in at least two dimensions, and a pattern matching mechanism for matching of a taken microscope image and registered template images, it is possible to provide a function of automatic access to the noted pattern using pattern matching, without an operator needing to perform an operation.

A focused ion beam device of the present invention is preferably a scanning electron microscope, and by providing a sample stage drive mechanism capable of movement in at least two dimensions and changing inclination, and means for storing a series of operation programs from slicing machining to tilting of the sample stage, access to a noted pattern of a sliced section and shape measurement of the noted pattern, it is possible to automatically measure shape of a pattern formed in the sliced section from machining of the sliced section of the sample without the need for an operator to be present. Moreover, since it is possible to prepare this program simply by inputting parameters and data into basic software, it can be executed according to respective programs even if there are different functions.

What is claimed is:

1. A scanning microscope, comprising: means for generating and scanning an energized beam across a sample surface; a detector for detecting particles emitted by the sample in response to irradiation of the sample surface with the energized beam; a computer for generating an image on a display based on an output of the detector; automatic brightness control means for automatically controlling the brightness of an image displayed on the display based on information obtained from the overall image; means for designating an average brightness of a specific local region of the image; and means for suspending operation of the automatic brightness control means to control brightness of the overall image based on the average brightness of the specific local region so that when the specific local region of the sample is designated in a first image obtained using a relatively low magnification factor, a second image comprising an image of the specific local region may be displayed at a relatively high magnification factor to observe a detailed pattern of the specific local region.

2. A scanning microscope according to claim 1; further comprising a sample stage drive mechanism for moving the sample in at least two dimensions; means for storing plural template images; and a pattern matching mechanism for matching a stored template image to a pattern contained in the second image to enable automatic location of a desired pattern in the specific local region.

3. A scanning microscope according to claim 2; wherein the sample stage drive mechanism is capable of inclining the sample; and further comprising means for storing a series of programs for automatically performing a plurality of operations in sequence, the series of operations comprising machining the sample to produce a cross section, tilting the sample to enable viewing of the cross section, locating a desired pattern in the cross section, and measuring a shape of the desired pattern.

4. A method for controlling brightness of a magnified image obtained using a microscope, the method comprising the steps of:
 displaying a first microscope image of an overall region of a sample at a relatively low magnification, the overall region including a specific local region surrounded by a peripheral region;
 adjusting the brightness of the first microscope image to make the specific local region more distinct and clearer than the peripheral region;
 increasing a magnification factor of the microscope to a relatively high magnification while maintaining the adjusted brightness; and
 displaying a second microscope image of the specific local region at the relatively high magnification and at the adjusted brightness.

5. A method according to claim 4; wherein the step of displaying a first microscope image is carried out at a brightness based on brightness information obtained from the overall region.

6. A method according to claim 4; wherein the step of adjusting the brightness comprises adjusting the brightness of the first microscope image to enable observation of a detailed pattern of the specific local region that cannot be observed without brightness adjustment.

7. A method according to claim 6; wherein the specific local region comprises a cross-sectional region of the sample.

8. A method according to claim 4; wherein the specific local region comprises a cross-sectional region of the sample.

9. A method according to claim 4; wherein the step of adjusting the brightness comprises adjusting the brightness of the first microscope image based solely on characteristics of the specific local region without regard to characteristics of the peripheral region.

10. A method according to claim 4; wherein the step of displaying a first microscope image is carried out at a brightness automatically determined based on the brightness of the overall region.

* * * * *